US010239229B2

(12) United States Patent
Nguyen et al.

(10) Patent No.: US 10,239,229 B2
(45) Date of Patent: Mar. 26, 2019

(54) SYSTEM AND METHOD FOR GENERATING FORMATION CORES WITH REALISTIC GEOLOGICAL COMPOSITION AND GEOMETRY

(71) Applicant: HALLIBURTON ENERGY SERVICES, INC., Houston, TX (US)

(72) Inventors: Philip D. Nguyen, Houston, TX (US); Loan K. Vo, Houston, TX (US); Brian D. Mock, Kingwood, TX (US); Aaron Christopher Kralovetz, Rosharon, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 225 days.

(21) Appl. No.: 15/111,748

(22) PCT Filed: Feb. 18, 2014

(86) PCT No.: PCT/US2014/016958
§ 371 (c)(1),
(2) Date: Jul. 14, 2016

(87) PCT Pub. No.: WO2015/126369
PCT Pub. Date: Aug. 27, 2015

(65) Prior Publication Data
US 2016/0332329 A1 Nov. 17, 2016

(51) Int. Cl.
*B28B 17/00* (2006.01)
*E21B 41/00* (2006.01)
(Continued)

(52) U.S. Cl.
CPC .......... *B28B 17/0081* (2013.01); *B28B 1/001* (2013.01); *B33Y 10/00* (2014.12);
(Continued)

(58) Field of Classification Search
CPC .......................... B28B 17/0081; G01N 23/045
See application file for complete search history.

(56) References Cited

U.S. PATENT DOCUMENTS

| 4,575,330 A | 3/1986 | Hull |
| 5,597,520 A | 1/1997 | Smalley et al. |
| (Continued) | | |

FOREIGN PATENT DOCUMENTS

| WO | 2005097476 A2 | 10/2005 |
| WO | 2012073089 A1 | 6/2012 |
| WO | 2013043908 A1 | 3/2013 |

OTHER PUBLICATIONS

International Search Report and Written Opinion; PCT Application No. PCT/US2014/016958; dated Nov. 12, 2014.

*Primary Examiner* — Joseph A Miller, Jr.
(74) *Attorney, Agent, or Firm* — Polsinelli PC

(57) ABSTRACT

Systems, methods, and computer-readable storage devices for scanning a retrieved geological core sample to produce a digital file representing the core sample. Then the digital file is transmitted to a three-dimensional printer that can execute the digital file to make a geologically, chemically, and structurally equivalent replica of the retrieved geological core sample. The three-dimensional printer can optionally combine a base geological material with one or more additives or with an inert binding agent layer by layer as three-dimensional pixels. The replica core sample can then be used for testing or for other purposes at a greatly reduced cost than retrieving multiple actual core samples. Further, the replica core sample can be reproduced at virtually any location rather than transporting an actual core sample.

3 Claims, 6 Drawing Sheets

(51) Int. Cl.
- *B33Y 10/00* (2015.01)
- *B33Y 50/00* (2015.01)
- *B33Y 30/00* (2015.01)
- *B28B 1/00* (2006.01)
- *E21B 25/00* (2006.01)
- *G01N 21/3563* (2014.01)
- *G01N 23/046* (2018.01)
- *G01N 23/20* (2018.01)
- *G01N 23/2251* (2018.01)

(52) U.S. Cl.
CPC ............... *B33Y 30/00* (2014.12); *B33Y 50/00* (2014.12); *E21B 25/00* (2013.01); *E21B 41/00* (2013.01); *G01N 21/3563* (2013.01); *G01N 23/046* (2013.01); *G01N 23/20* (2013.01); *G01N 23/2251* (2013.01)

(56) References Cited

U.S. PATENT DOCUMENTS

| | | |
|---|---|---|
| 6,164,850 A | 12/2000 | Speakman |
| 6,813,594 B2 | 11/2004 | Guertin et al. |
| 7,569,273 B2 | 8/2009 | Bredt et al. |
| 8,070,473 B2 | 12/2011 | Kozlak |
| 2009/0259446 A1 | 10/2009 | Zhang et al. |
| 2012/0224755 A1* | 9/2012 | Wu .................. G06T 17/00 382/131 |
| 2012/0277996 A1 | 11/2012 | Hurley et al. |
| 2013/0180327 A1 | 7/2013 | Frederick |
| 2013/0259190 A1 | 10/2013 | Walls et al. |
| 2013/0301794 A1 | 11/2013 | Grader et al. |
| 2014/0278106 A1* | 9/2014 | Mallet .................. G01V 99/005 702/2 |
| 2014/0379119 A1* | 12/2014 | Sciacchitano ....... G05B 19/4099 700/182 |

* cited by examiner

SYSTEM AND METHOD FOR GENERATING FORMATION CORES WITH REALISTIC GEOLOGICAL COMPOSITION AND GEOMETRY

CROSS-REFERENCE TO RELATED APPLICATIONS

This application is a national stage entry of PCT/US2014/016958 filed Feb. 18, 2014, said application is expressly incorporated herein in its entirety.

TECHNICAL FIELD

The present disclosure relates to producing replica core samples that reproduce the chemical, geological, and structural characteristics of an actual core sample, such as via a three-dimensional printer that combines a base material with additives and/or an inert binding agent in an additive layer-by-layer manner.

DESCRIPTION OF RELATED ART

During exploration for mineral, oil, or gas resources, geologists often extract core samples from a target area by drilling into the Earth. The cost and time associated with extracting such core samples is often prohibitive. Accordingly, core samples are extremely valuable and can often cost more than their weight in gold to retrieve. Some geological tests performed on core samples are destructive, essentially consuming the core sample by the end of the test. Some of these tests can evaluate how the core sample reacts to fluids to be pumped into a well. The high cost of obtaining core samples is an impediment to mineral and oil exploration as the scarcity of available core sample often restricts core sample testing.

BRIEF DESCRIPTION OF THE DRAWINGS

Embodiments of the present disclosure will now be described by way of example with reference to attached figures, wherein.

DETAILED DESCRIPTION

Figure 1:
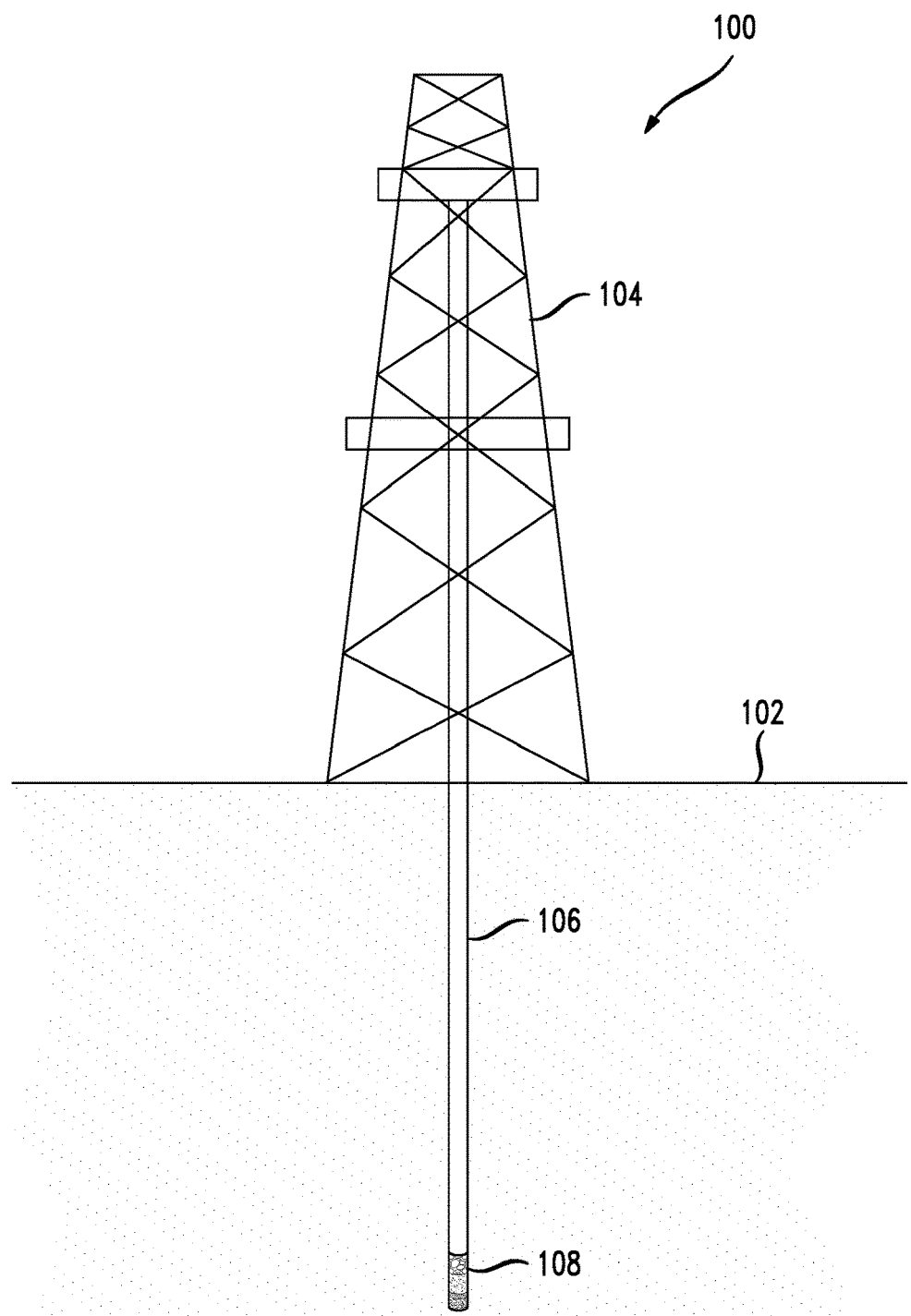
FIG. 1 illustrates a side view of a drilling rig for retrieving a core sample from beneath the surface of the earth.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

The present disclosure describes methods and apparatus for producing replica core samples that reproduce the geological, chemical, and structural characteristics of an original core sample retrieved from the earth. The present disclosure can also apply to other, non-geological core samples. The concepts disclosed herein can be implemented using various core sample extraction hardware, scanning equipment to analyze an extracted core sample, and a three-dimensional printer that can selectively combine a base material with additives and/or a binding agent as three-dimensional pixels. These replica core samples provide realistic geological compositions and geometry. An equivalent replica core sample duplicates in sufficient detail the characteristics of the original core sample so that testing, such as flow testing, can be performed on the replica core sample. Further, additional copies of the replica core sample can be fabricated on demand, and data files describing how to produce the replica can be stored, sorted, transmitted and the like as with any digital file. Various examples of these principles are set forth below.

It should be understood that most current, off-the-shelf 3D printers will need to be modified to accommodate most, if not all, of these embodiments. For example, an off-the-shelf 3D printer may be modified to add or enhance capability for functionalities such as various viscosity flows, mixing, temperature control, pressure control, dispensing apparatus (liquid or particle selection and distribution), a rotating printing area, and so forth.

FIG. 1 illustrates a side view 100 of a drilling rig 104 for retrieving a core sample 108 from beneath the surface 102 of the earth. The drilling rig 104 drills a hole 106 and extracts a core sample 108 via the hole 106.

Figure 2:
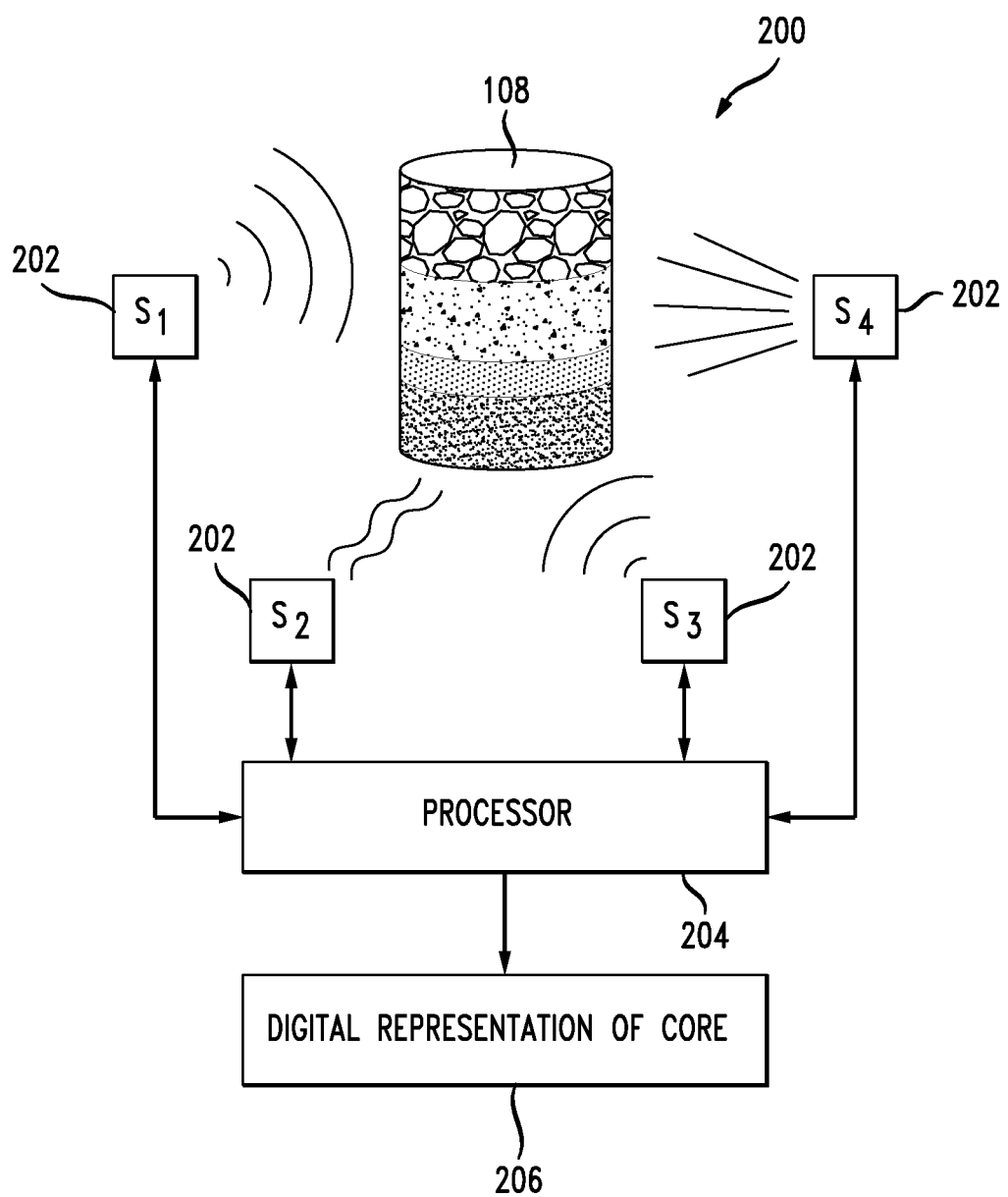
FIG. 2 illustrates a schematic diagram of an example system embodiment for scanning a retrieved core sample.

FIG. 2 illustrates a schematic diagram 200 of an example system embodiment for scanning a retrieved core sample 108. When an actual core sample 108, formation core, or other geological structure is obtained, various sensors $S_1 \ldots S_4$ 202 scan the core sample 108 to determine a basic chemical composition, structural composition, and other details. The sensors 202 can include sensors for performing x-ray diffraction, x-ray computed tomography, near infrared spectroscopy, a scanning electron microscope, energy dispersive x-ray spectroscopy, or other sensing or imaging technologies. The exact types and combinations of these sensors 202 may vary depending on the desired characteristics of the core sample 108 to record, cost of the sensors, cost of operating the sensors, time constraints, and the like. The processor 204 can obtain, via the sensors 202, details, cross-section structural properties, and mineral compositions for each three-dimensional "pixel" unit of the core sample 108. The processor 204 can store these details, structural properties, and mineral compositions as a digital representation 206 of the core sample 108.

Figure 3:
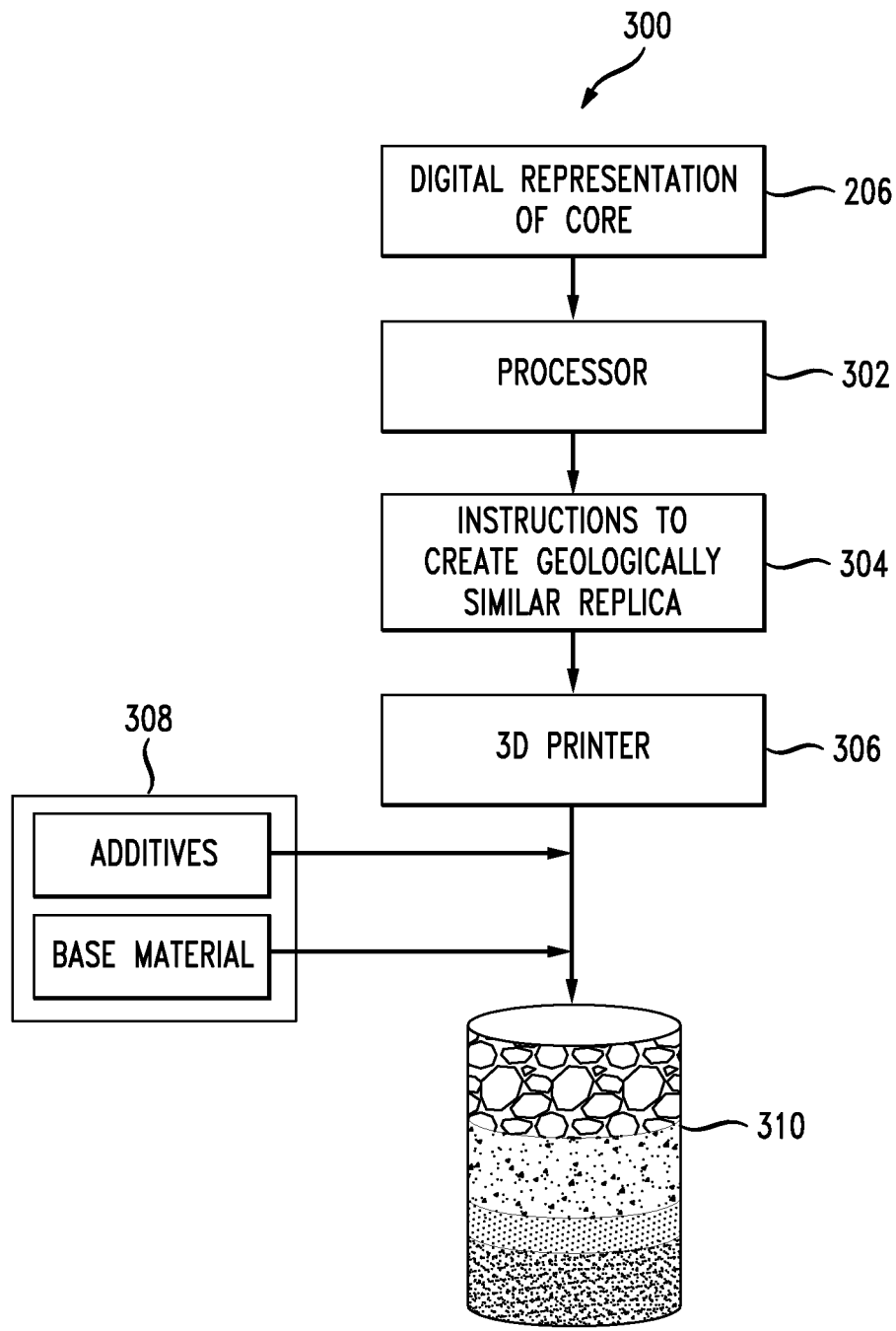
FIG. 3 illustrates a schematic diagram of an example system embodiment for producing a geologically similar replica of the retrieved core sample.

FIG. 3 illustrates a schematic diagram 300 of an example system embodiment for producing a geologically similar replica of the retrieved core sample based on the digital representation 206. A processor 302 receives the digital representation 206 of the core sample, which can be represented in a markup language such as XML, or a digital file describing pixels, coordinates, and pixel details. The digital representation 206 can be binary data or textual data. The digital representation can also include additional parameters, instructions, or metadata. For example, the metadata can describe details of the source of the core sample, such as the geographic location, a drilling rig, an organization that retrieved the core sample, a date stamp of when the core sample was retrieved, a depth from which the core sample was retrieved, and the like. The additional parameters can indicate a pixel size, orientation, and shape, acceptable tolerances for producing a replica core, and so forth. The instructions can provide explicit conditions, for example, for producing the replica core as required by a particular desired subsequent test on the replica core, or as indicated by a user.

The processor 302 can read the digital representation 206 of the core sample, and adapt the digital representation 206 to a set of instructions 304 for a three-dimensional printer 306 to create a geologically similar replica of the core sample. The processor 302 can produce different sets of instructions 304 for different types of three-dimensional printers 306 in different file formats or instruction formats. The processor 302 can use different hardware or software plugins or software drivers that can be updated or added as new types of three-dimensional printers 306 or new file formats are developed.

The three-dimensional printer 306 can combine base materials and additives 308 to produce a replica core sample 310. The additives can include materials such as silicon, aluminum, calcium, iron, magnesium oxide, carbonates, and common clay minerals. The three-dimensional printer 306 can also combine an inert binding agent to replicate various structural elements of the core sample according to the instructions 304. The three-dimensional printer 306 constructs the replica core sample 310 layer by layer with the chemical additives and inert binding agents included with the base material at the appropriate locations or pixels within the replica core sample 310. The base material for the three-dimensional printer 306 can be plaster, for example. The additives can be mixed with the base material before or after depositing the base material in layers. The three-dimensional printer 306 can utilize powders of additives deposited in layers via inkjet-like heads. The replica core sample 310 reproduces the original core sample 108 within desired tolerances. While the replica core sample 310 may not be identical to the original core sample 108, the replica core sample 310 is sufficiently similar to provide accurate or reliable data for desired testing, such as flow testing.

In one embodiment, after subjecting the core sample through a computed tomography scanner, the digital information of an untreated core is provided to allow the three-dimensional printer 306 to generate just the porous network of the core. In another embodiment, after subjecting the acidized core sample through a computed tomography scanner, the digital information of the acidized core is provided to allow the three-dimensional printer 306 to generate the wormholes and their network created by acidizing. In yet another embodiment, after subjecting the core sample through the computed tomography scanner, the digital information of the core sample that has been hydraulic fractured in a laboratory environment is provided to allow the three-dimensional printer 306 to generate the propped fractures and branches created in the block post-testing. In yet another embodiment, after subjecting the proppant pack through the computed tomography scanner before and after fluid treatment (e.g., fracturing fluid, consolidation treatment resin and the like), the digital information of proppant pack before and after treatment is captured to allow the three-dimensional printer to generate the porous network of the pack, allowing an expert to determine the damage or plugging resulted from the fluid treatment. The system can distribute digital representations of the replica core samples pre- and post-testing so that other technicians/experts can produce and examine the results personally without being on-site. This approach can save costs in transportation of either technicians/experts or core samples. Further, for tests that are destructive of the original core sample, this allows the original core sample and the post-testing core sample to be replicated as many times and in as many locations as desired.

With this approach, the three-dimensional printer 306 can regenerate "almost identical" replica cores 310 to enhance testing capability. The replica cores 310 can reproduce various sand sizes and fine particulates with similar permeability, porosity, and/or porous structure as compared to the original core sample 108. The cohesion between grains and any tendency of fine migration are incorporated based on the information from the scanners 202. The chemical make-up of the replica core 310 is similar to the original core sample 108, as are physical structures.

Figure 4:
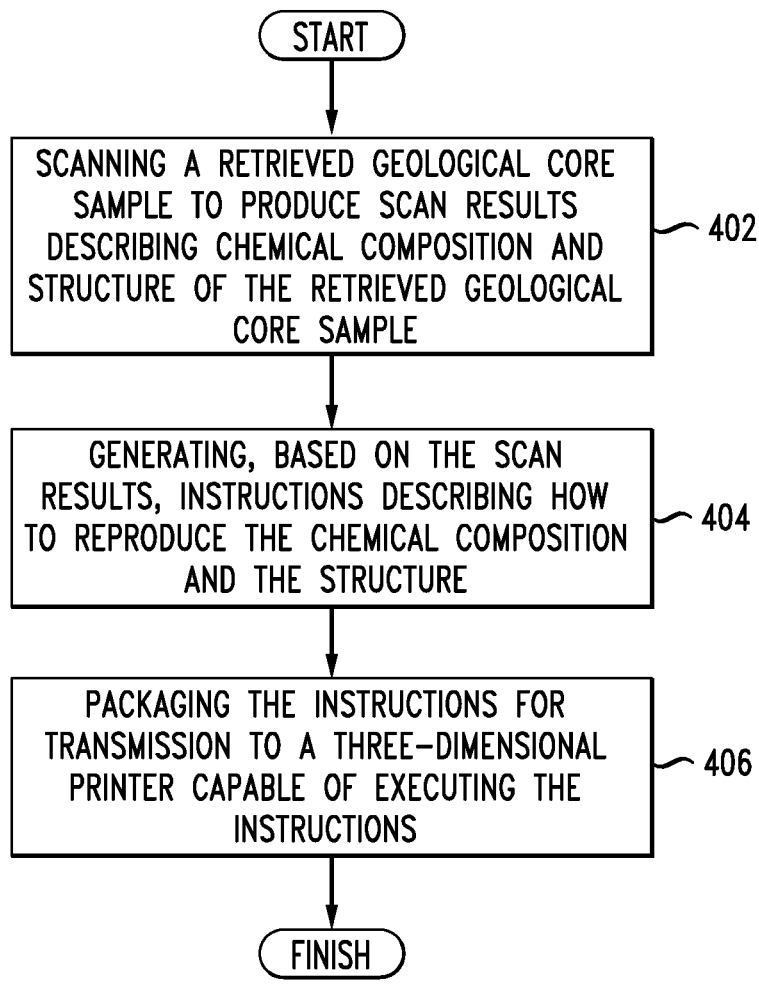
FIG. 4 illustrates a flowchart of a first example method embodiment.

Having discussed various details of producing a replica core 310, the disclosure turns now to FIG. 4 which illustrates a flowchart of a first example method embodiment for producing instructions for the three-dimensional printer 306. These steps can be implemented in other orders, combinations, or permutations, that include or exclude these or other steps. A system implementing this method can scan a retrieved geological core sample to produce scan results describing chemical composition of the retrieved geological core sample (402). The scan results can include a collection of three-dimensional pixels, wherein each three-dimensional pixel describes structural properties and mineral composition of a respective portion of the retrieved geological core sample, and wherein the collection of three-dimensional pixels collectively describes structural properties and mineral composition of the retrieved geological core sample. The scan results can include a collection of non-cube shaped, three-dimensional regions, wherein each non-cube shaped, three-dimensional region describes structural properties and mineral composition of a respective portion of the retrieved geological core sample, and wherein the collection of non-cube shaped, three-dimensional regions collectively describes structural properties and mineral composition of the retrieved geological core sample. The scan results can also describe a structure of the retrieved geological core sample.

The system can generate, based on the scan results, instructions describing how to reproduce the chemical composition (404) and optionally the structure or other details of the retrieved geological core sample. The instructions can further describe base geological components and additive geological components such as silicon, aluminum, calcium, iron, magnesium oxide, carbonate, or clay minerals. The system can package the instructions for transmission to a three-dimensional printer capable of executing the instructions (406).

Figure 5:
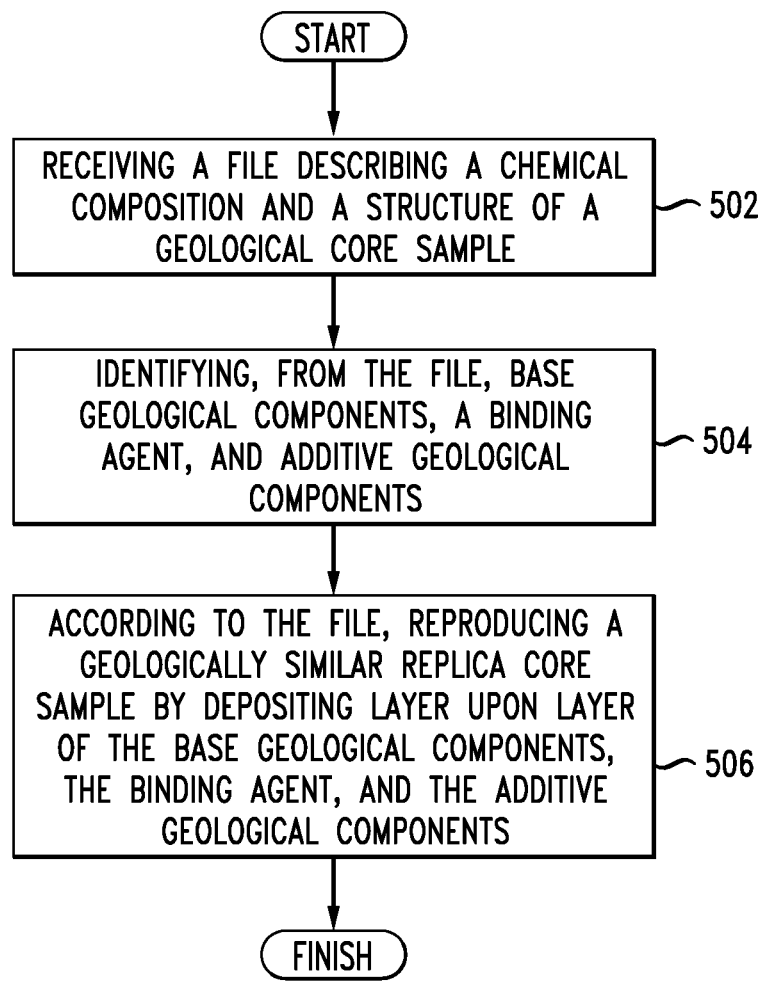
FIG. 5 illustrates a flowchart of a second example method embodiment.

FIG. 5 illustrates a flowchart of a second example method embodiment for receiving the instructions and producing the replica core sample. The system can receive a file describing a chemical and structural composition of a geological core sample (502). The file can be in a file format specifically intended for a three-dimensional printer. The system can identify, from the file, base geological components and additive geological components (504). The file can specify geological attributes. Then the three-dimensional printer can identify, based on the geological attributes, a suitable base geological component and a suitable additive geological component that, when combined, are within a threshold similarity to the geological attributes indicated in the file.

According to the file, the system can reproduce a geologically similar replica core sample by depositing layer upon layer of the base geological components mixed with additive geological components (506), and optionally with an inert binding agent. The geologically similar replica core sample can be reproduced by depositing layer upon layer via a plaster-based three-dimensional printer using powders for the additive geological components and the inert binding agents. The three-dimensional printer can also include various liquids of specific pH levels in the layers as part of the three-dimensional printing process.

The system can optionally receive a scaling factor, such as indicated in the file or manually entered by a human operator. Alternatively, the three-dimensional printer may be required to scale the original dimensions for the core sample down to fit within the maximum print size for the three-dimensional printer. Then the three-dimensional printer can reproduce the geologically similar replica core sample further according to the scaling factor, such that the geologically similar replica core sample is a different size than the original geological core sample. Similarly, the file can provide a high-resolution data set of the original core sample, and the system can reduce the resolution down to match or to be within the maximum print resolution or other limitations of the three-dimensional printer.

In yet another method embodiment illustrating the entire process from scanning the original core sample to producing the replica core sample, the system can scan a retrieved geological core sample to produce scan results describing a chemical composition and a structure of the retrieved geological core sample. Then, the system can generate, based on the scan results, input data for a three dimensional printer describing how to reproduce the chemical composition and the structure. The system can execute the input data, via the three dimensional printer, to produce a geologically similar replica core sample by depositing layer upon layer of base geological components, additive geological components, and a binding agent.

Some of the benefits of the approaches set forth herein are that the digital information of core samples can be saved, compared, and searched, as with virtually any digital information. The digital information can be transmitted anywhere in the world to allow construction of one or more cores or structures at different testing facilities. The chemical make-up and physical structure of the replica cores have similar properties to those of the original core sample. This approach can save costs and time as fewer actual cores can be retrieved. The replica cores allow experts to examine the porous network of the cores, both before and after fluid treatment. Experts can also examine the wormhole structure in the replica core after acidizing treatment, or the structure of propped fracture in the replica core after lab fracturing treatment. Experts can examine the pore structures and any potential damage or plugging in the treated proppant pack.

Figure 6:
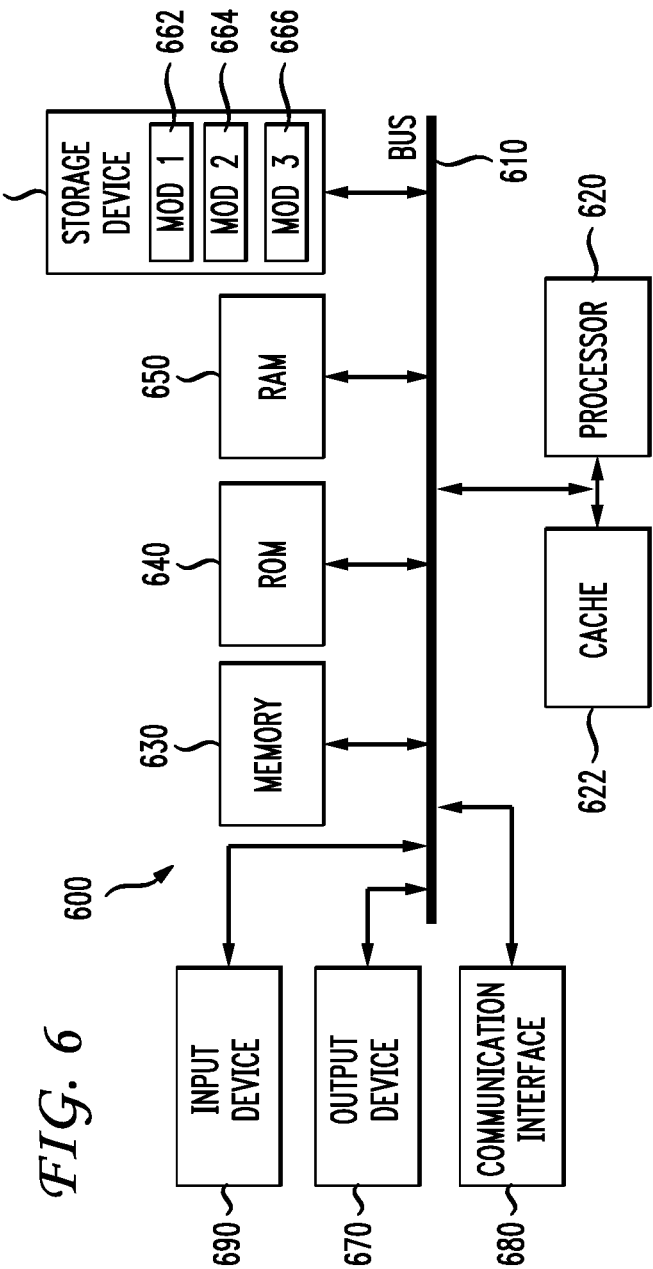
FIG. 6 illustrates a schematic diagram of an example system embodiment including functional descriptions.

The disclosure now turns to FIG. 6, which illustrates a general system 600, all or part of which can be used to implement the principles disclosed herein. With reference to FIG. 6, an exemplary system and/or computing device 600 includes a processing unit (for example, a central processing unit (CPU) or processor) 620 and a system bus 610 that couples various system components, including the system memory 630 such as read only memory (ROM) 640 and random access memory (RAM) 650, to the processor 620. The system 600 can include a cache 622 of high-speed memory connected directly with, in close proximity to, or integrated as part of the processor 620. The system 600 copies data from the memory 630 and/or the storage device 660 to the cache 622 for quick access by the processor 620. In this way, the cache provides a performance boost that avoids processor 620 delays while waiting for data. These and other modules can control or be configured to control the processor 620 to perform various operations or actions.

Other system memory 630 can be available for use as well. The memory 630 can include multiple different types of memory with different performance characteristics. It can be appreciated that the disclosure may operate on a computing device 600 with more than one processor 620 or on a group or cluster of computing devices networked together to provide greater processing capability. The processor 620 can include any general purpose processor and a hardware module or software module, such as module 1 662, module 2 664, and module 3 666 stored in storage device 660, configured to control the processor 620 as well as a special-purpose processor where software instructions are incorporated into the processor. The processor 620 can be a self-contained computing system, containing multiple cores or processors, a bus, memory controller, cache and the like. A multi-core processor can be symmetric or asymmetric. The processor 620 can include multiple processors, such as a system having multiple, physically separate processors in different sockets, or a system having multiple processor cores on a single physical chip. Similarly, the processor 620 can include multiple distributed processors located in multiple separate computing devices, but working together such as via a communications network. Multiple processors or processor cores can share resources such as memory 630 or the cache 622, or can operate using independent resources. The processor 620 can include one or more of a state machine, an application specific integrated circuit (ASIC), or a programmable gate array (PGA) including a field PGA.

The system bus 610 can be any of several types of bus structures including a memory bus or memory controller, a peripheral bus, and a local bus using any of a variety of bus architectures. A basic input/output (BIOS) stored in ROM 640 or the like, may provide the basic routine that helps to transfer information between elements within the computing device 600, such as during start-up. The computing device 600 can further include storage devices 160 or computer-readable storage media such as a hard disk drive, a magnetic disk drive, an optical disk drive, tape drive, solid-state drive, RAM drive, removable storage devices, a redundant array of inexpensive disks (RAID), hybrid storage device, or the like. The storage device 660 can include software modules 662, 664, 666 for controlling the processor 620. The system 600 can include other hardware or software modules. The storage device 660 can be connected to the system bus 610 by a drive interface. The drives and the associated computer-readable storage devices can provide nonvolatile storage of computer-readable instructions, data structures, program modules and other data for the computing device 600. In one aspect, a hardware module that performs a particular function can include the software component stored in a tangible computer-readable storage device in connection with the necessary hardware components, such as the processor 620, bus 610, display 670 and the like to carry out a particular function. In another aspect, the system can use a processor and computer-readable storage device to store instructions which, when executed by the processor, cause the processor to perform operations, a method or other specific actions. The basic components and appropriate variations can be modified depending on the type of device, such as whether the device 100 is a small, handheld computing device, a desktop computer, or a computer server. When the processor 620 executes instructions to perform "operations", the processor 120 can perform the operations directly and/or facilitate, direct, or cooperate with another device or component to perform the operations.

Although the exemplary embodiment(s) described herein employs the hard disk 660, other types of computer-readable storage devices which can store data that are accessible by a computer, such as magnetic cassettes, flash memory cards, digital versatile disks (DVDs), cartridges, random access memories (RAMs) 650, read only memory (ROM) 640, a cable containing a bit stream and the like may also be used in the exemplary operating environment. Tangible computer-readable storage media, computer-readable storage devices, or computer-readable memory devices, expressly exclude media such as transitory waves, energy, carrier signals, electromagnetic waves, and signals per se.

To enable user interaction with the computing device 600, an input device 690 represents any number of input mechanisms, such as a microphone for speech, a touch-sensitive screen for gesture or graphical input, keyboard, mouse, motion input, speech and the like. An output device 670 can also be one or more of a number of output mechanisms known to those of skill in the art. In some instances, multimodal systems enable a user to provide multiple types of input to communicate with the computing device 600. The communications interface 680 generally governs and manages the user input and system output. There is no restriction on operating on any particular hardware arrangement and therefore the basic hardware depicted may easily be substituted for improved hardware or firmware arrangements as they are developed.

For clarity of explanation, the illustrative system embodiment is presented as including individual functional blocks including functional blocks labeled as a "processor" or processor 620. The functions these blocks represent can be provided through the use of either shared or dedicated hardware, including, but not limited to, hardware capable of executing software and hardware, such as a processor 620, that is purpose-built to operate as an equivalent to software executing on a general purpose processor. For example the functions of one or more processors presented in FIG. 6 can be provided by a single shared processor or multiple processors. (Use of the term "processor" should not be construed to refer exclusively to hardware capable of executing software.) Illustrative embodiments can include microprocessor and/or digital signal processor (DSP) hardware, read-only memory (ROM) 640 for storing software performing the operations described below, and random access memory (RAM) 650 for storing results. Very large scale integration (VLSI) hardware embodiments, as well as custom VLSI circuitry in combination with a general purpose DSP circuit, can also be provided.

The logical operations of the various embodiments can be implemented as: (1) a sequence of computer implemented steps, operations, or procedures running on a programmable circuit within a general use computer; (2) a sequence of computer implemented steps, operations, or procedures running on a specific-use programmable circuit; and/or (3) interconnected machine modules or program engines within the programmable circuits. The system 600 shown in FIG. 6 can practice all or part of the recited methods, can be a part of the recited systems, and/or can operate according to instructions in the recited tangible computer-readable storage devices. Such logical operations can be implemented as modules configured to control the processor 620 to perform particular functions according to the programming of the module. For example, FIG. 6 illustrates three modules Mod1 662, Mod2 664 and Mod3 666 that are modules configured to control the processor 620. These modules may be stored on the storage device 660 and loaded into RAM 650 or memory 630 at runtime or may be stored in other computer-readable memory locations.

One or more parts of the example computing device 600, up to and including the entire computing device 600, can be virtualized. For example, a virtual processor can be a software object that executes according to a particular instruction set, even when a physical processor of the same type as the virtual processor is unavailable. A virtualization layer or a virtual "host" can enable virtualized components of one or more different computing devices or device types by translating virtualized operations to actual operations. Ultimately however, virtualized hardware of every type can implemented or executed by some underlying physical hardware. Thus, a virtualization compute layer can operate on top of a physical compute layer. The virtualization compute layer can include one or more of a virtual machine, an overlay network, a hypervisor, virtual switching, and any other virtualization application.

The processor 620 can include all types of processors disclosed herein, including a virtual processor. However, when referring to a virtual processor, the processor 620 can include the software components associated with executing the virtual processor in a virtualization layer and underlying hardware necessary to execute the virtualization layer. The system 100 can include a physical or virtual processor 620 that receives instructions stored in a computer-readable storage device, which cause the processor 620 to perform certain operations. When referring to a virtual processor 620, the system also includes the underlying physical hardware executing the virtual processor 620.

Embodiments within the scope of the present disclosure may also include tangible and/or non-transitory computer-readable storage devices for carrying or having computer-executable instructions or data structures stored thereon. Devices or a storage medium can be part of a system for controlling the raising, lowering, or other movement control of a tool 302 and the retrieval and processing of the acoustic array data received by the sensors on the tool 302. Such tangible computer-readable storage devices can be any available device that can be accessed by a general purpose or special purpose computer, including the functional design of any special purpose processor as described above. By way of example, and not limitation, such tangible computer-readable devices can include RAM, ROM, EEPROM, CD-ROM or other optical disk storage, magnetic disk storage or other magnetic storage devices, or any other device which can be used to carry or store desired program code in the form of computer-executable instructions, data structures, or processor chip design. When information or instructions are provided via a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable storage devices.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules can include routines, programs, components, data structures, objects, and the functions inherent in the design of special-purpose processors and the like that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Other embodiments of the disclosure can be practiced in network computing environments with many types of computer system configurations, including personal computers, hand-held devices, multi-processor systems, microprocessor-based or programmable consumer electronics, network PCs, minicomputers, mainframe computers, and the like. Embodiments can also be practiced in distributed computing environments where tasks are performed by local and remote processing devices that are linked (either by hard-wired links, wireless links, or by a combination thereof) through a communications network. In a distributed computing environment, program modules can be located in both local and remote memory storage devices.

The various embodiments described above are provided by way of illustration only and should not be construed to limit the scope of the disclosure. For example, the principles herein can apply to geologic source material other than core samples, and can also extend to 'core sample' like materials, such as samples retrieved by boring into a tree. In these situations, it may be risky to bore multiple holes into a very old tree to examine tree rings or fluid flow, and a biologically similar 3D-printed core sample replicas may reduce the need to obtain such core samples. Therefore, many such details are neither shown nor described. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the embodiments described above may be modified within the scope of the appended claims. Claim language reciting "at least one of" a set indicates that one member of the set or multiple members of the set satisfy the claim.

We claim:

1. A method comprising:
    scanning, by one or more sensors, a retrieved geological core sample to produce scan results describing chemical composition and structural composition of the retrieved geological core sample;
    generating, via a processor and based on the scan results, instructions describing base geological components, additive geological components, a combination of the base geological components and the additive geological components, and how to reproduce the chemical composition and the structural composition of the retrieved geological core sample in a replica core sample using the base geological components, additive geological components, and the combination of the base geological components and the additive geological components,
    the additive geological components comprising at least one of silicon, aluminum, calcium, iron, magnesium oxide, carbonate, or clay minerals,
    the base geological components comprising plaster,
    the scan results comprising a collection of three-dimensional pixels, and wherein each three-dimensional pixel describes structural properties and mineral composition of a respective portion of the retrieved geological core sample, and
    the collection of three-dimensional pixels collectively describing structural properties and mineral composition of the retrieved geological core sample;
    packaging the instructions to be in a file having a format compatible with a three-dimensional printer capable of executing the instructions to produce the replica core sample which has substantially similar chemical composition and structural composition as the retrieved geological core sample;
    transmitting the file to the three-dimensional printer;
    identifying, at a corresponding location of each of the three-dimensional pixels by the three-dimensional printer, one or more suitable base geological components and one or more suitable additive geological components from the base geological components and the additive geological components based on the instructions;
    mixing, for the corresponding location of each of the three dimensional pixels by the three-dimensional printer, the one or more suitable base geological components and the one or more suitable additive geological components to form the chemical composition of the retrieved geological core sample;
    ejecting, at the corresponding location of each of the three dimensional pixels by the three-dimensional printer, the suitable base geological components mixed with the suitable additive geological components through one or more inkjet-like heads of the three-dimensional printer; and
    reproducing, by the three-dimensional printer, a geologically similar replica core sample by depositing layer upon layer of the suitable base geological components mixed with the suitable additive geological components based on the instructions.

2. The method of claim 1, wherein the one or more sensors includes at least one of x-ray diffraction, x-ray computed tomography, near infrared spectroscopy, a scanning electron microscope, or energy dispersive x-ray spectroscopy.

3. The method of claim 1, wherein the scan results comprise a collection of non-cube shaped, three-dimensional regions, wherein each non-cube shaped, three-dimensional region describes structural properties and mineral composition of a respective portion of the retrieved geological core sample, and wherein the collection of non-cube shaped, three-dimensional regions collectively describes structural properties and mineral composition of the retrieved geological core sample.

* * * * *